United States Patent
Umebayashi

(10) Patent No.: US 9,750,647 B2
(45) Date of Patent: Sep. 5, 2017

(54) WEARING ARTICLE AND PRODUCTION METHOD THEREFOR

(75) Inventor: Toyoshi Umebayashi, Settsu (JP)

(73) Assignee: ZUIKO CORPORATION (JP)

( * ) Notice: Subject to any disclaimer, the term of this patent is extended or adjusted under 35 U.S.C. 154(b) by 770 days.

(21) Appl. No.: 14/127,668

(22) PCT Filed: Jun. 5, 2012

(86) PCT No.: PCT/JP2012/003677
§ 371 (c)(1),
(2), (4) Date: Dec. 19, 2013

(87) PCT Pub. No.: WO2012/176386
PCT Pub. Date: Dec. 27, 2012

(65) Prior Publication Data
US 2014/0115757 A1 May 1, 2014

(30) Foreign Application Priority Data
Jun. 23, 2011 (JP) .................................. 2011-139194

(51) Int. Cl.
*A61F 13/49* (2006.01)
*A61F 13/15* (2006.01)
(Continued)

(52) U.S. Cl.
CPC ........ *A61F 13/49* (2013.01); *A61F 13/15723* (2013.01); *A61F 13/15739* (2013.01);
(Continued)

(58) Field of Classification Search
None
See application file for complete search history.

(56) References Cited

U.S. PATENT DOCUMENTS

| 6,027,484 A | 2/2000 | Romare |
| 6,500,161 B1 | 12/2002 | Freiburger et al. |

(Continued)

FOREIGN PATENT DOCUMENTS

| DE | 198 13 334 | 9/1999 |
| JP | 2005-230313 | 9/2005 |

(Continued)

OTHER PUBLICATIONS

European Appl. No. 12 802 911.3—Search Report dated Oct. 17, 2014.
International Search Report dated Sep. 11, 2012.

*Primary Examiner* — Barbara J Musser
(74) *Attorney, Agent, or Firm* — Gerald E. Hespos; Michael J. Porco; Matthew T. Hespos

(57) ABSTRACT

A method for producing a wearing article includes conveying a front-abdominal-portion forming strip and a rear-dorsal-portion forming strip; dividing the front-abdominal-portion forming strip being conveyed, along a dividing line parallel to a width direction thereof; holding a relative positional relationship between two segments of the front-abdominal-portion forming strip on both sides of the dividing line; within a period of implementation of the step of holding, detachably attaching a first attaching-detaching member to the front-abdominal-portion forming strip in such a manner as to cover the dividing line, thereby restricting a relative displacement between the segments of the front-abdominal-portion forming strip on both sides of the dividing line; joining the front-abdominal-portion forming strip and a front region of a crotch portion together; and joining the rear-dorsal-portion forming strip and a rear region of the crotch portion together.

6 Claims, 9 Drawing Sheets

(51) Int. Cl.
*A61F 13/56* (2006.01)
*A61F 13/64* (2006.01)

(52) U.S. Cl.
CPC .. *A61F 13/15756* (2013.01); *A61F 13/15764* (2013.01); *A61F 13/15804* (2013.01); *A61F 13/4906* (2013.01); *A61F 13/5633* (2013.01); *A61F 13/5638* (2013.01); *A61F 13/5644* (2013.01); *A61F 13/64* (2013.01)

(56) References Cited

U.S. PATENT DOCUMENTS

| | | | |
|---|---|---|---|
| 8,029,634 B2* | 10/2011 | Widlund | A61F 13/565 156/204 |
| 2004/0138635 A1* | 7/2004 | Sorenson | A61F 13/15593 604/385.01 |
| 2012/0061016 A1* | 3/2012 | Lavon | A61F 13/15593 156/226 |

FOREIGN PATENT DOCUMENTS

| | | |
|---|---|---|
| JP | 2005-230330 | 9/2005 |
| JP | 2005-270390 | 10/2005 |
| JP | 2006-175104 | 7/2006 |
| JP | 2006-340862 | 12/2006 |

\* cited by examiner

WEARING ARTICLE AND PRODUCTION METHOD THEREFOR

TECHNICAL FIELD

The present invention relates to a wearing article and a production method therefor.

BACKGROUND ART

Heretofore, there has been known a refastenable absorbent article as disclosed, for example, in the following JP2003-520627A. The absorbent article described in the JP2003-520627A comprises a front portion disposed on a front torso of a wearer in use, a back portion disposed on a back of the wearer, and a crotch portion connecting the front portion and the back portion together. The crotch portion has a distal end region extending up to a front abdominal region of the wearer, and an inner surface of the front portion is detachably attached to an outer surface of the distal end region of the crotch portion through a hook-and-loop fastener and others. The front portion can be broken into a right, first lateral section and a left, second lateral section through a perforation line.

Based on the above configuration, the absorbent article described in the Patent Document 1 can improve a close-to-the-body fit about a wearer's waist. Specifically, a level of tightness of the front and back portions to a wearer's waist can be adjusted by breaking the front portion into a first lateral section and a second lateral section through a perforation line, and attaching the first and second lateral sections, respectively, to desired positions of the distal end region of the crotch portion through hook-and-loop fasteners.

In this case, each of the first and second lateral sections to be obtained by breaking through the perforation line is formed using a non-woven fabric.

However, in the absorbent article described in the JP2003-520627A has a problem that it is difficult to break the front portion into the first and second lateral sections, because it is necessary to break the front portion comprised of a non-woven fabric, into the first and second lateral sections through the perforation line.

More specifically, a large number of fibers constituting the first and second lateral sections are intricately entangled at perforation non-forming areas on the perforate line, so that a large force is required to disentangle the fibers.

It is an object of the present invention to provide a wearing article capable of readily adjusting a close-to-the-body fit about a wearer's waist, and a production method for the wearing article.

SUMMARY OF THE INVENTION

In order to solve the above problem, the present invention provides a method of producing a wearing article, wherein the wearing article comprises a front abdominal portion disposed on a front abdominal region of a wearer in a worn state, a rear dorsal portion disposed on a rear dorsal region of the wearer in the worn state, and a crotch portion connecting the front abdominal portion and the rear dorsal portion together in the worn state. The method comprises: an strip conveying step of conveying a first strip for forming one of the front abdominal portion and the a rear dorsal portion, and a second strip for forming the other, in such a manner as to allow respective longitudinal directions of the first and second strips to become parallel to each other, while applying, to each of the first and second strips, a tension along the longitudinal direction thereof; a dividing step of dividing the first strip being conveyed, along a dividing line along a width direction of the first strip; a holding step of holding a relative positional relationship between two segments of the first strip on both sides of the dividing line; a restricting step of, within a period of implementation of the holding step, detachably attaching a first attaching-detaching member to the first strip in such a manner as to cover the dividing line, thereby restricting a relative displacement between the segments of the first strip on both sides of the dividing line; a first-end-region joining step of joining the first attaching-detaching member and a first end region of the crotch portion together; a second-end-region joining step of joining the second strip and a second end region of the crotch portion on a side opposite to the first end region; a folding step of folding an intermediate region of the crotch portion, thereby superimposing the first and second strips on each other; a side-sealing step of joining the superimposed first and second strips together on a lateral side of the folded crotch portion; and a cutting step of cutting the superimposed first and second strips in such a manner that a joined section formed in the side-sealing step is left on each of both sides of the folded crotch portion.

The present invention also provides a method of producing a wearing article, wherein the wearing article comprises a front abdominal portion disposed on a front abdominal region of a wearer in a worn state, a rear dorsal portion disposed on a rear dorsal region of the wearer in the worn state, and a crotch portion connecting the front abdominal portion and the rear dorsal portion together in the worn state. The method comprises: an strip conveying step of conveying a first strip for forming one of the front abdominal portion and the a rear dorsal portion, and a second strip for forming the other, in such a manner as to allow respective longitudinal directions of the first and second strips to become parallel to each other, while applying, to each of the first and second strips, a tension along the longitudinal direction thereof; a dividing step of dividing the first strip being conveyed, along a dividing line along a width direction of the first strip; a holding step of holding a relative positional relationship between two segments of the first strip on both sides of the dividing line; a restricting step of, within a period of implementation of the holding step, detachably attaching a first end region of the crotch portion to the first strip in such a manner as to cover the dividing line, thereby restricting a relative displacement between the segments of the first strip on both sides of the dividing line; a second-end-region joining step of joining a second end region of the crotch portion on a side opposite to the first end region to the second strip; a folding step of folding an intermediate region of the crotch portion, thereby superimposing the first and second strips on each other; a side-sealing step of joining the superimposed first and second strips together on a lateral side of the folded crotch portion; and a cutting step of cutting the superimposed first and second strips in such a manner that a joined section formed in the side-sealing step is left on each of both sides of the folded crotch portion.

Further, the present invention provides a wearing article produced by either one of the above methods.

Furthermore, the present invention provides a wearing article which comprises: a front abdominal portion disposed on a front abdominal region of a wearer in a worn state; a rear dorsal portion disposed on a rear dorsal region of the wearer in the worn state; and a crotch portion having a front end region connected to the front abdominal portion and a rear end region connected to the rear dorsal portion, in the worn state, wherein the front abdominal portion or the rear dorsal portion has a dividing line along which the front abdominal portion or the rear dorsal portion is preliminarily divided into a right segment and a left segment, and wherein each of the right and left segments is attachable and detachable with respect to the front or rear end region of the crotch portion.

The present invention can provide a wearing article capable of readily adjusting a close-to-the-body fit about a wearer's waist, and a production method for the wearing article.

DESCRIPTION OF EMBODIMENTS

Figure 1:
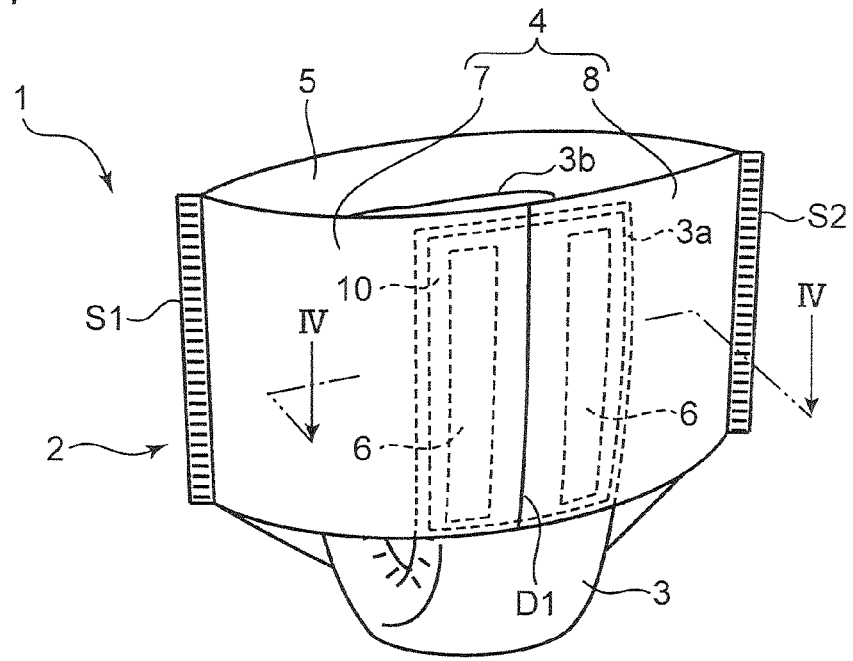
FIG. 1 is a perspective view illustrating an overall configuration of a disposable diaper according to one embodiment of the present invention.

With reference to the accompanying drawings, an embodiment of the present invention will now be described. The following embodiments will be shown by way of specific example of the present invention, and are not intended to limit a technical scope of the present invention.

Referring to FIGS. 1 to 4, a disposable diaper 1 as one example of a wearing article, according to one embodiment of the present invention, comprises: an annular-shaped waist band 2 disposed on a waist region of a wearer in a worn state; a crotch portion 3 disposed on a crotch region of the wearer in the worn state; and a first attaching-detaching member 10 and a pair of second attaching-detaching members 6 for detachably attaching a front end region of the crotch portion 3 to the waist portion 2 therethrough.

The waist band 2 comprises a front abdominal portion 4 disposed on a front abdominal region of the wearer in the worn state, and a rear dorsal portion 5 disposed on a rear dorsal region of the wearer in the worn state. A right edge of the front abdominal portion 4 and a right edge of the rear dorsal portion 5 are joined through a side-sealed section S1. Further, a left edge of the front abdominal portion 4 and a left edge of the rear dorsal portion 5 are joined through a side-sealed section S2. The front abdominal portion 4 has a dividing line D1 along which the front abdominal portion 4 is preliminarily divided into a right, front abdominal segment 7 and a left, front abdominal segment 8. Each of the front abdominal portion 4 and the rear dorsal portion 5 is stretchable in a right-left direction. Specifically, each of the front abdominal portion 4 and the rear dorsal portion 5 may be made of a material having elasticity in its own (elastic non-woven fabric), or may be formed by placing an elastic member between a pair of sheets comprised of a non-woven fabric, in a stretched state. The elastic member may be made of polyurethane, natural rubber, or thermoplastic resin. Further, the elastic member may be formed in a string-like or ribbon-like shape.

The crotch portion 3 connects the front abdominal portion 4 and the rear dorsal portion 5 together. Specifically, an outer surface of a front region 3a of the crotch portion 3 is detachably attached to an inner surface (a surface facing to a wearer's skin) of the front abdominal portion 4 through the attaching-detaching members 6, 10 to be described below. On the other hand, an outer surface of a rear region 3b of the crotch portion 3 is joined to an inner surface of the rear dorsal portion 5. The crotch portion 3 in this embodiment is capable of absorbing urine or the like of a wearer. Specifically, the crotch portion 3 comprises a liquid-permeable top sheet provided on an inner side thereof, a liquid-impermeable cover sheet provided on an outer side thereof, an absorbent core provided between the top and cover sheet, although illustration is omitted. Therefore, urine or the like penetrating through the top sheet is absorbed by the absorbent core. The top sheet may be formed using a liquid-permeable non-woven fabric or mesh sheet. The cover sheet may be formed using a breathable (air-permeable) polyethylene film, a water-shedding and breathable non-woven fabric, or a laminated film thereof. The absorbent core may be formed by laminating fluffs obtained by subjecting roll pulp to crushing and fibrillation. In this case, a superabsorbent polymer may be mixed in the fluffs.

The first attaching-detaching member 10 and each of the pair of second attaching-detaching members 6 are hook-and-loop fastener elements attachable and detachable with respect to each other. Specifically, as illustrated in detail in FIG. 4, the first attaching-detaching member 10 comprises a tape substrate 10a joined to the outer surface of the crotch portion 3 through an adhesive H2, and a loop element 10b provided on an outer surface of the tape substrate 10a. On the other hand, the pair of second attaching-detaching members 6 are provided, respectively, on the right, front abdominal segment 7 and the left, front abdominal segment 8. Specifically, each of the second attaching-detaching members 6 comprises a tape substrate 6a joined to the inner surface of the right, front abdominal segment 7 or the left, front abdominal segment 8 through an adhesive H1, and a hook element 6b provided on an inner surface of the tape substrate 6a. When the loop element 10b and the hook element 6b are lockingly fastened to each other, the right, front abdominal segment 7 and the left, front abdominal segment 8 are detachably attached to the front region 3a of the crotch portion 3.

Figure 2:
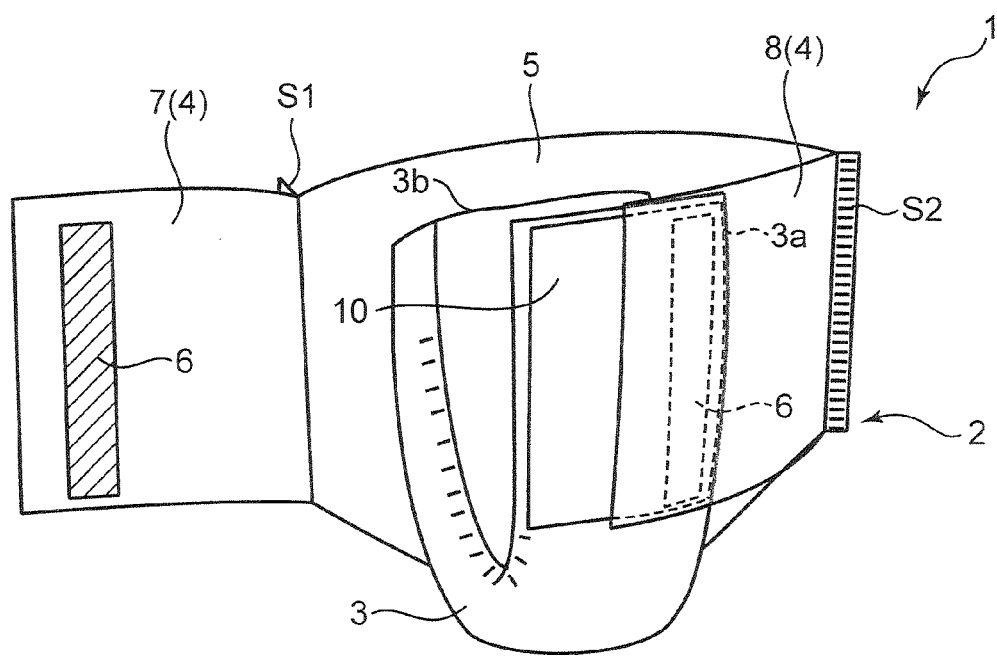
FIG. 2 is a perspective view illustrating a state in which a right abdominal segment of a front abdominal portion of the disposable diaper in FIG. 1 is developed.
Figure 3:
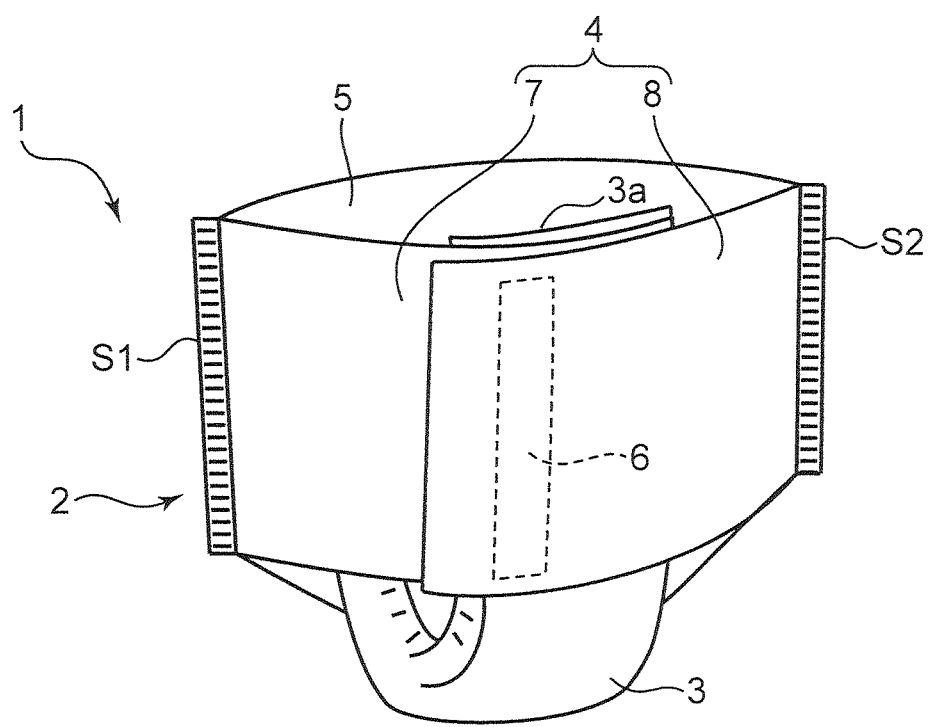
FIG. 3 is a perspective view illustrating a state in which the front abdominal portion of the disposable diaper in FIG. 1 is developed and then re-attached to a crotch portion.
Figure 4:
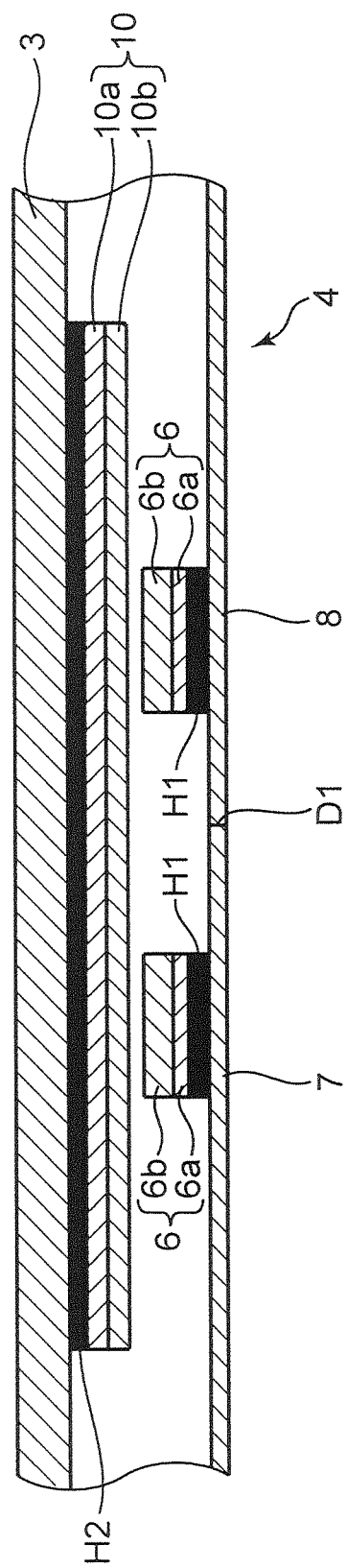
FIG. 4 is a sectional view taken along the line IV-IV in FIG. 1.

As described above, in the disposable diaper 1, the front abdominal portion 4 is preliminarily divided into the right, front abdominal segment 7 and the left, front abdominal segment 8 along the dividing line D1, and each of the right, front abdominal segment 7 and the left, front abdominal segment 8 is attachable and detachable with respect to the crotch portion 3. Thus, for example, as illustrated in FIG. 2, only through an operation of detaching the right, front abdominal segment 7 from the crotch portion 3, and re-attaching the right, front abdominal segment 7 to the crotch portion 3 at a position spaced apart from the left, front abdominal segment 8, a level of tightness of the waist band 2 to a wearer's waist can be lowered by the spacing. Differently, the right, front abdominal segment 7 and/or the left, front abdominal segment 8 may be detached from the crotch portion 3, and then the hook element(s) 6b thereof may be attached to the crotch portion 3 in such a manner that a spacing between the hook elements 6b of the two segments becomes narrower than that in an initial state. In this case, the level of tightness of the waist band 2 to the wearer's waist can be increased. In this embodiment, the waist band 2 has an outer surface comprised of a non-woven fabric, as illustrated in FIG. 3. Thus, one of the right, front abdominal segment 7 and the left, front abdominal segment 8 can be attached to an outer surface of the other, so as to further increase the level of tightness of the waist band 2 to the wearer's waist.

In this embodiment, the dividing line D1 is formed in the front abdominal portion 4. Alternatively, the dividing line D1 may be formed in the rear dorsal portion 5. Although this embodiment has been described by taking a hook-and-loop fastener as an example of the first attaching-detaching member 10 and the second attaching-detaching members 6, the present invention is not limited thereto. Specifically, any other mutually attachable-detachable elements may be employed as the first attaching-detaching member 10 and each of the pair of second attaching-detaching members 6.

Figure 5:
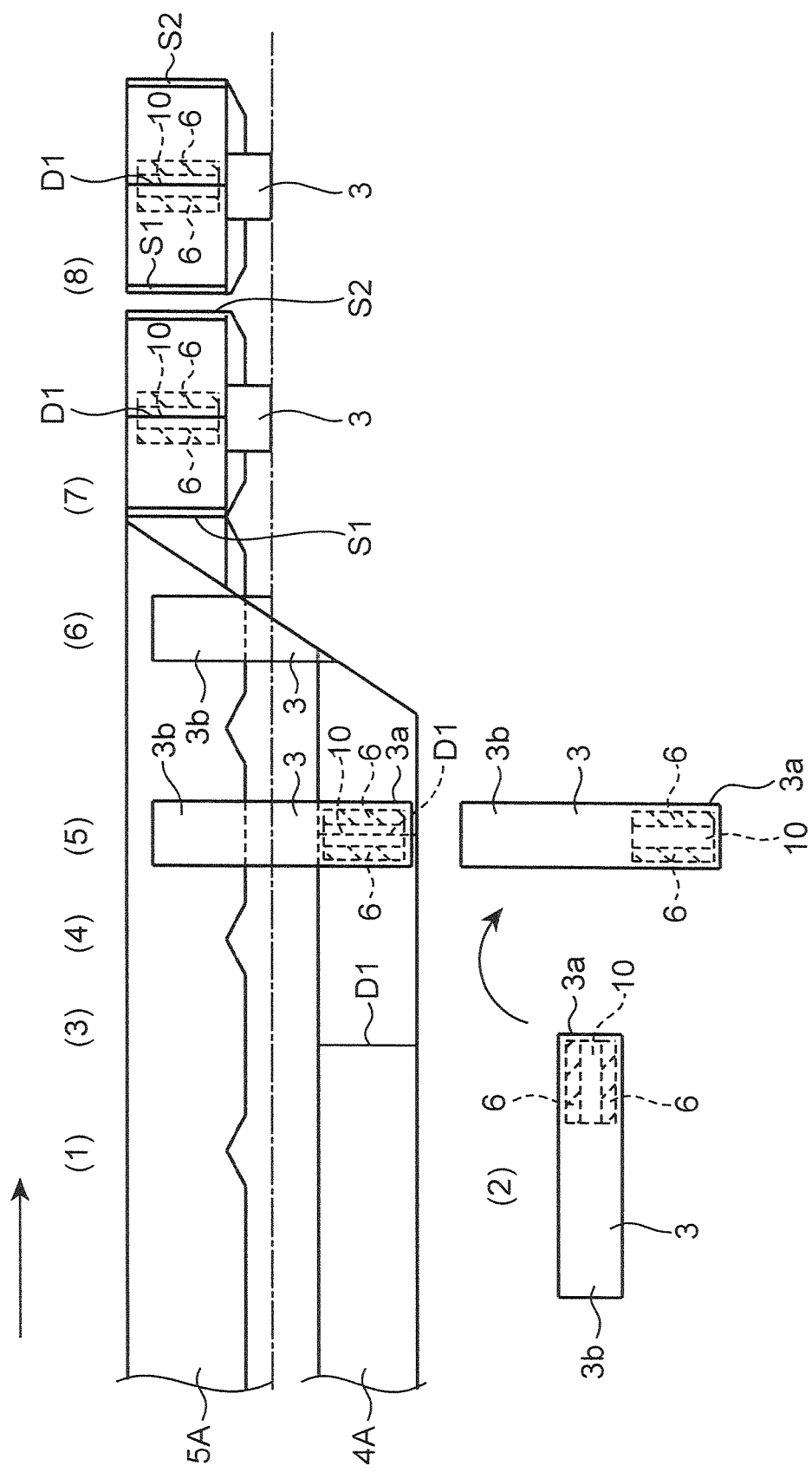
FIG. 5 is a process diagram illustrating a production method for the disposable diaper in FIG. 1.

With reference to FIG. 5, a production method for the above disposable diaper 1 will be described below.

A production method according to one embodiment of the present invention comprises a strip conveying step (1), a crotch portion forming step (2), a dividing step (3), a holding step (4), a crotch portion attaching step (5), a the folding step (6), a side sealing step (7), and a cutting step (8).

In the strip conveying step (1), a front-abdominal-portion forming strip (first strip) 4A for forming the front abdominal portion 4 and a rear-dorsal-portion forming strip (second strip) 5A for forming the rear dorsal portion 5 are conveyed in such a manner as to allow respective longitudinal directions of the first and second strips 4A, 5A to become parallel to each other, while applying, to each of the first and second strips 4A, 5A, a tension along the longitudinal direction thereof. The strip conveying step (1) will be continued until the cutting step (8) to be described below is completed.

In the crotch portion forming step (2), a work-in-process is formed which comprises the crotch portion 3, the first attaching-detaching member 10 and the pair of second attaching-detaching members 6. Specifically, in the crotch portion forming step (2), the crotch portion 3 is formed by sandwiching an absorbent core between a top sheet and a cover sheet, although illustration of these components is omitted. Further, in the crotch portion forming step (2), a subassembly obtained by assembling the pair of second attaching-detaching members 6 to the first attaching-detaching member 10 is prepared (preparing step). The subassembly is obtained by lockingly fastening each of the hook elements 6b of the pair of second attaching-detaching members 6 to the loop element 10b of the first attaching-detaching member 10, in such a manner that the pair of second attaching-detaching members 6 are spaced apart from each other in a width direction of the crotch portion 3. Then, in the crotch portion forming step (2), the tape substrate 10a (see FIG. 4) of the first attaching-detaching member 10 of the subassembly is bonded to the front region 3a of the crotch portion 3 by the adhesive H2 (first-end-region joining step). In a period before the crotch portion attaching step (5) to be described below is started, the crotch portion forming step (2) is implemented concurrently with the steps (1), (3) and (4).

In the dividing step (3), the dividing line D1 is formed in the front-abdominal-portion forming strip 4A along its width direction. Consequently, the front-abdominal-portion forming strip 4A is divided in its longitudinal direction.

In the holding step (4), a relative positional relationship between segments of the front-abdominal-portion forming strip 4A on both sides of the dividing line D1 is held. Specifically, the holding step (4) is started simultaneously together with or before the dividing step (3), and discontinued simultaneously together with or after the crotch portion attaching step (restricting step) (5) to be described below. This makes it possible to prevent the segments of the front-abdominal-portion forming strip 4A on both sides of the dividing line D1 from becoming spaced apart from each other, even in a situation where a tension is applied to the front-abdominal-portion forming strip 4A due to the strip conveying step (1).

In the crotch portion attaching step (5), the front region 3a (the first attaching-detaching member 10) of the crotch portion 3 is detachably attached to the front-abdominal-portion forming strip 4A, and the rear region 3b of the crotch portion 3 is joined to the rear-dorsal-portion forming strip 5A. Specifically, in the crotch portion attaching step (5), the tape substrates 6a of the pair of second attaching-detaching members 6 attached to the crotch portion 3 are joined, respectively, to the segments of the front-abdominal-portion forming strip 4A on both sides of the dividing line D1, by the adhesive H1 (see FIG. 4) (restricting step). Thus, the pair of second attaching-detaching members 6 are fixed to the front-abdominal-portion forming strip 4A, so that a relative displacement between the segments on both sides of the dividing line D1 is restricted by the first attaching-detaching member 10 fixedly attached to the second attaching-detaching members 6. In FIG. 5, the attaching-detaching members 6, 10 are attached to an area of the front-abdominal-portion forming strip 4A excluding widthwise opposite edge regions thereof. Alternatively, the attaching-detaching members 6, 10 may be attached over the widthwise entire area of the front-abdominal-portion forming strip 4A. In this case, it becomes possible to more reliably prevent the relative displacement between the segments on both sides of the dividing line D1. Further, in the crotch portion attaching step (5), the rear region 3b of the crotch portion 3 is bonded onto the rear-dorsal-portion forming strip 5A by a non-illustrated adhesive.

Figure 6:
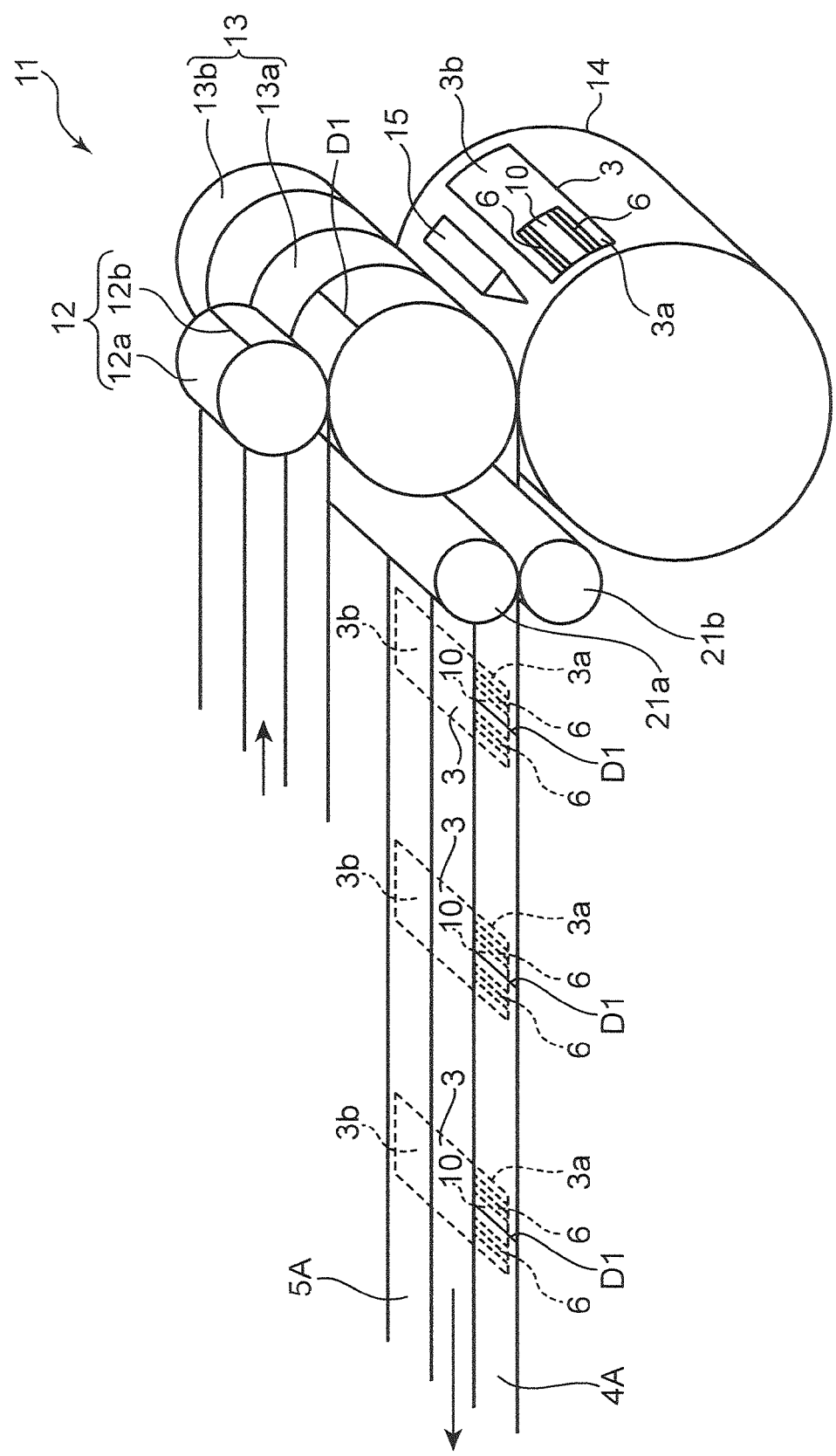
FIG. 6 is a perspective view illustrating an absorbent body attaching apparatus for use in a production process in FIG. 5.
Figure 7:
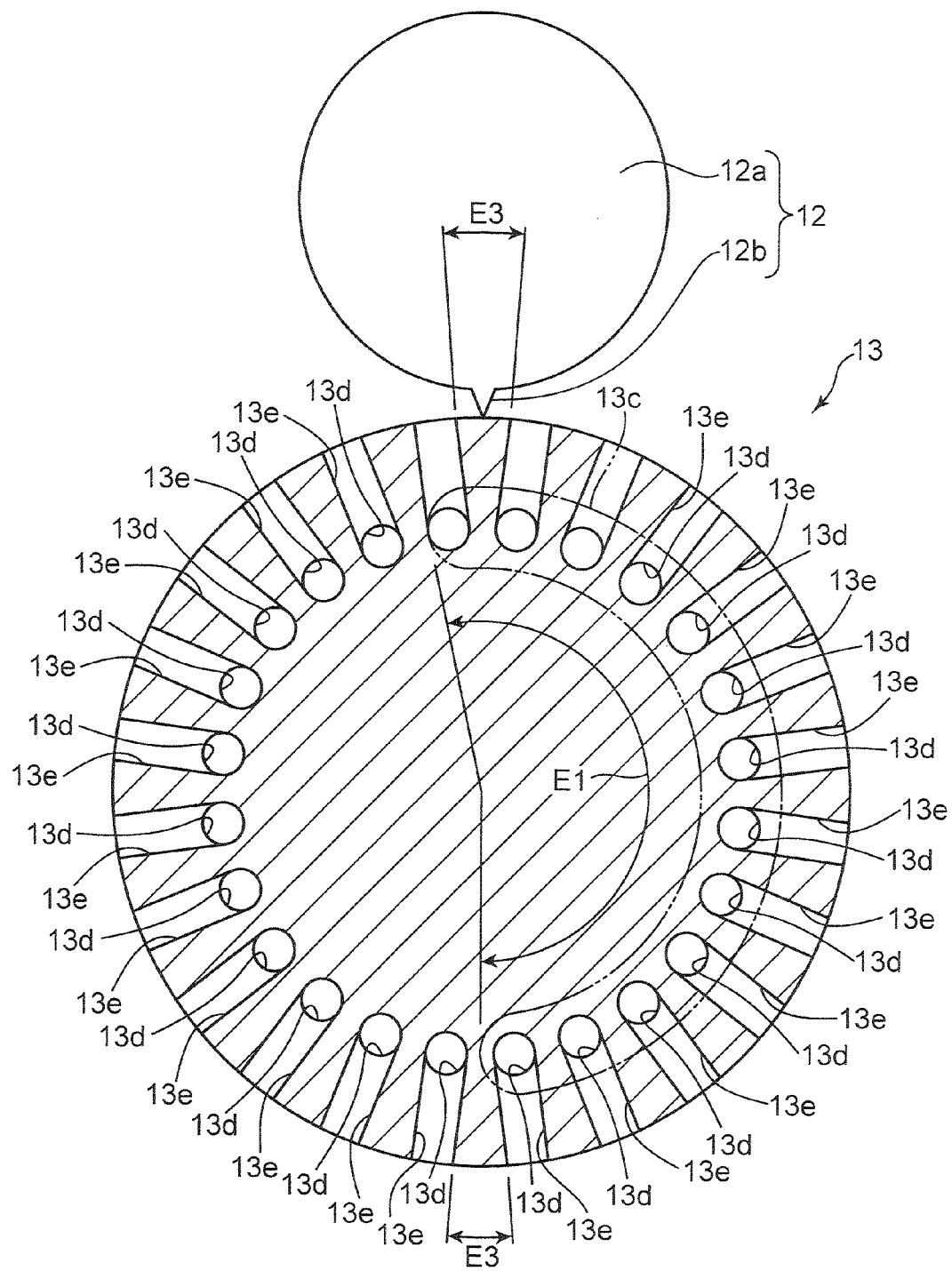
FIG. 7 is a sectional side view of a dividing roller and a holding roller in FIG. 6.

With reference to FIG. 6 and FIG. 7, a crotch portion attaching apparatus 11 for implementing the steps (3) to (5) will be described below.

The crotch portion attaching apparatus 11 comprises: a dividing roller 12 for dividing the front-abdominal-portion forming strip 4A; a strip holding roller 13 for holding the front-abdominal-portion forming strip 4A and the rear-dorsal-portion forming strip 5A; a crotch portion holding roller 14 for holding the crotch portion 3; a nozzle 15 for supplying an adhesive; and pressing rollers 21a, 21a for pressing therebetween the crotch portion 3 and each of the strips 4A, 5A.

The dividing roller 12 comprises a roller body 12a rotatable about a non-illustrated rotational axis, and a dividing blade 12b provided on an outer peripheral surface of the roller body 12a. The dividing blade 12b is configured to divide the front-abdominal-portion forming strip 4A, in cooperation with the strip holding roller 13 to be described below.

The strip holding roller 13 is configured to hold the front-abdominal-portion forming strip 4A and the rear-dorsal-portion forming strip 5A in such a manner as to allow respective longitudinal directions of the strips 14A, 15A to become parallel to each other. Specifically, the strip holding roller 13 comprises a holding barrel portion 13a rotatable about a rotational axis parallel to the rotational axis of the dividing roller 12, and a stationary portion 13b fixed to become immovable irrespective of rotation of the holding barrel portion 13a.

The holding barrel portion 13a is capable of holding the front-abdominal-portion forming strip 4A and the rear-dorsal-portion forming strip 5A, on an outer peripheral surface thereof. Specifically, as illustrated in FIG. 7, the holding barrel portion 13a is internally provided with a plurality of communication passages 13d each extending along an axial direction of the holding barrel portion 13a and opened in one end face the holding barrel portion 13a, and a plurality of suction holes 13e each extend from a respective one of the communication passages 13d to outside in a radial direction and opened in the outer peripheral surface of the holding barrel portion 13a. The stationary portion 13b is configured to produce a negative pressure within a specific part of the communication passages 13d and the suction holes 13e located in an angular range E1 illustrated in FIG. 7. Specifically, the stationary portion 13b has an end face in slidable relation to and in close contact with the one end face of the holding barrel portion 13a in which the communication passages 13d are opened. The end face of the stationary portion 13b has an arc-shaped depressurization opening 13c opened in the angular range E1. A region of the end face of the stationary portion 13b in an angular range other than that of depressurization opening 13c is in airtight relation to and in close contact with the one end face of the holding barrel portion 13a. A non-illustrated suction source is connected to the depressurization opening 13c. Thus, when the non-illustrated suction source is activated, air within the specific communication passages 13d located in the angular range E1 is sucked via the depressurization opening 13c, so that a negative pressure is produced in the specific suction holes 13e connected to the specific communication passages 13d. As a result, the strips 4A, 5a located on a region of the outer peripheral surface of the holding barrel portion 13a in the angular range E1 are hold. In this embodiment, in order to allow each of the strips 4A, 5a to be U-turned, each of the strips 4A, 5a is held along the outer peripheral surface of the holding barrel portion 13a, over a range of about one half of the circumference of the holding barrel portion 13a (about 190 degree). With respect to each of the communication passages 13d, a plurality of the suction holes 13e are provided in the axial direction of the holding barrel portion 13a. The plurality of suction holes 13e communicating with each of the communication passages 13d may be opened at different positions in a circumferential direction of the holding barrel portion 13a.

The angular range E1 is set to allow the holding of the strips 4A, 5A to be started before the dividing step (3) and ended simultaneously with end of the crotch portion attaching step (5). That is, the angular range E1 is a range between a position before a contact position with the dividing blade 12b and a press contact position with the crotch portion holding roller 14 to be described below. In this embodiment, a start point of the angular range E1 is set to a point before the dividing step (3). Alternatively, it may be set to the same point as a start point of the dividing step (3). Further, an end point of the angular range E1 is set to the same point as that of the crotch portion attaching step (5). Alternatively, it may be set to a point after the crotch portion attaching step (5).

In the embodiment, the dividing blade 12b of the dividing roller 12 is configured to be brought into contact with the outer peripheral surface of the holding barrel portion 13a every time the holding barrel portion 13a is rotated 180 degrees. Thus, the suction hole 13e is omitted in a rotational range E3 in which a contact with the dividing blade 12b occurs (see FIG. 7). This allows the front-abdominal-portion forming strip 4A to be reliably divided between the dividing blade 12b and the holding barrel portion 13a.

The crotch portion holding roller 14 is rotatable about a rotational axis parallel to the rotational axis of the strip holding roller 13 (holding barrel portion 13a). Specifically, the crotch portion holding roller 14 is rotatable while allowing an outer peripheral surface thereof to be kept in press contact with the outer peripheral surface of the strip holding roller 13 (holding barrel portion 13a). Further, the crotch portion holding roller 14 is capable of holding the crotch portion 3 on the outer peripheral surface thereof by an action of a non-illustrated suction source, as with the holding barrel portion 13a of the strip holding roller 13. Specifically, the crotch portion holding roller 14 is configured to hold the crotch portion 3 provided with the first attaching-detaching member 10 and the pair of second attaching-detaching members 6 after the crotch portion forming step (2).

The nozzle 15 is configured to apply an adhesive to respective surfaces of the pair of second attaching-detaching members 6 and a surface of the rear region 3b of the crotch portion 3 held by the crotch portion holding roller 14. The pair of second attaching-detaching members 6 applied with the adhesive, and the front-abdominal-portion forming strip 4A, are pressed between the strip holding roller 13 (holding barrel portion 13a) and the crotch portion holding roller 14. In the same manner, the rear region 3b of the crotch portion 3 applied with the adhesive, and the rear-dorsal-portion forming strip 5A, are pressed between the strip holding roller 13 (holding barrel portion 13a) and the crotch portion holding roller 14.

The pressing rollers 21a, 21b are designed to more reliably assure a bonding effect of the adhesive applied by the nozzle 15. Specifically, the pressing rollers 21a, 21a are rotatable while allowing respective outer peripheral surfaces thereof to be kept in press contact with each other. The crotch portion 3 and each of the front-abdominal-portion forming strip 4A and the rear-dorsal-portion forming strip 5A are pressed between the pressing rollers 21a, 21a, while interposing the first attaching-detaching member 10 and the pair of second attaching-detaching members 6 therebetween.

The use of the above crotch portion attaching apparatus 11 makes it possible to concurrently implement the restricting step of restricting a displacement between the segments on both sides of the dividing line D1 by the first attaching-detaching member 10, and a second-end-region joining step of joining the rear region 3b of the crotch portion 3 to the rear-dorsal-portion forming strip 5A.

Although the above strip holding roller 13 is configured to suck and hold the front-abdominal-portion forming strip 4A and the rear-dorsal-portion forming strip 5A, means for holding is not limited to suction. For example, in place of the strip holding roller 13, a strip holding roller 16 illustrated in FIGS. 8 to 10 may be employed.

Figure 8:
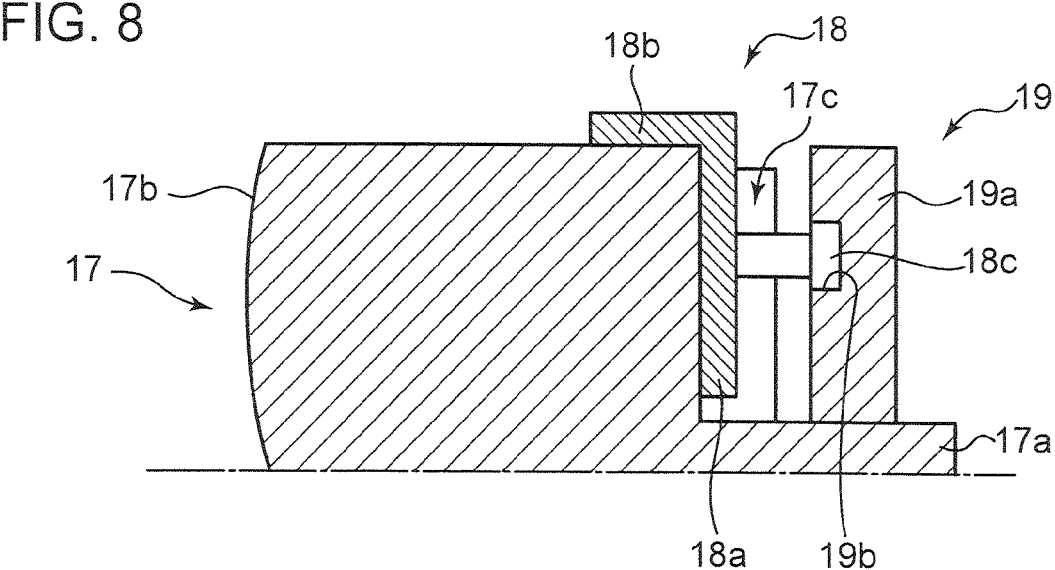
FIG. 8 is a front sectional view illustrating an example of a modified holding roller.
Figure 9:
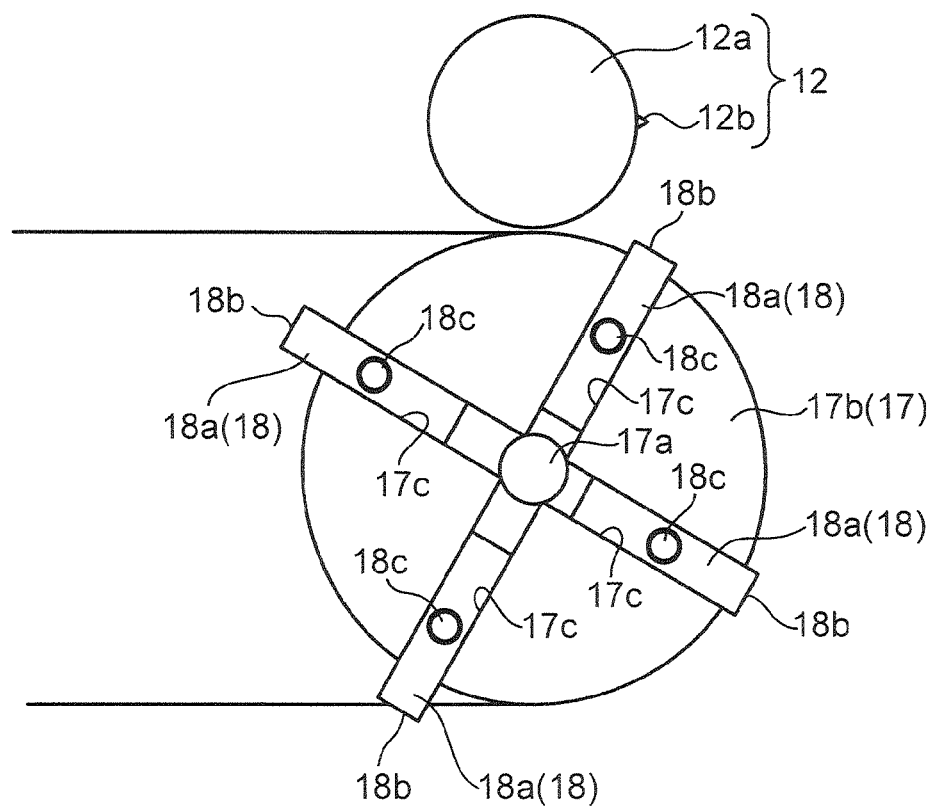
FIG. 9 is a side view illustrating the holding roller in FIG. 8, wherein a guide member thereof is omitted.

The strip holding roller 16 comprises: a roller body 17 around which the front-abdominal-portion forming strip 4A and the rear-dorsal-portion forming strip 5A are wound; eight holding members 18 (FIG. 9 illustrates four of them) for holding the strips 4A, 5A in cooperation with the roller body 17; and two guide members 19 (FIG. 8 illustrates one of them) for causing each of the holding members 18 to be relatively displaced with respect to the roller body 17.

The roller body 17 comprises a rotary shaft 17a, and a holding barrel 17b rotatable about the rotary shaft 17a. The holding barrel 17b has opposite end faces each formed with four sliding grooves 17c. The four sliding grooves 17c are formed at 90-degree intervals around the rotary shaft 17a. Each of the sliding grooves 17c extends radially from the rotary shaft 17a.

Each of the holding members 18 comprises: a fitting portion 18a slidably fitted in one of the sliding grooves 17c of the roller body 17; a holding portion 18b extending from the fitting portion 18a while bending at a right angle therewith; and a guide roller 18c protruding from the fitting portion 18a in a direction opposite to that of the holding portion 18b. The fitting portion 18a is slidingly movable in a diametrical direction of the roller body 17 along the sliding groove 17c. The holding portion 18b is disposed in opposed relation to an outer peripheral surface of the roller body 17. According to a sliding movement of the fitting portion 18a along the sliding groove 17c, the holding portion 18b is reciprocatingly movable between a hold position where it is located close to the outer peripheral surface of the holding barrel 17b, and a release position where it is located spaced apart from the outer peripheral surface of the holding barrel 17b. The guide roller 18c is inserted in an aftermentioned guide groove 19b of the guide member 19 in such a manner as to allow the holding members 18 to be moved between the hold position and the release position.

Figure 10:
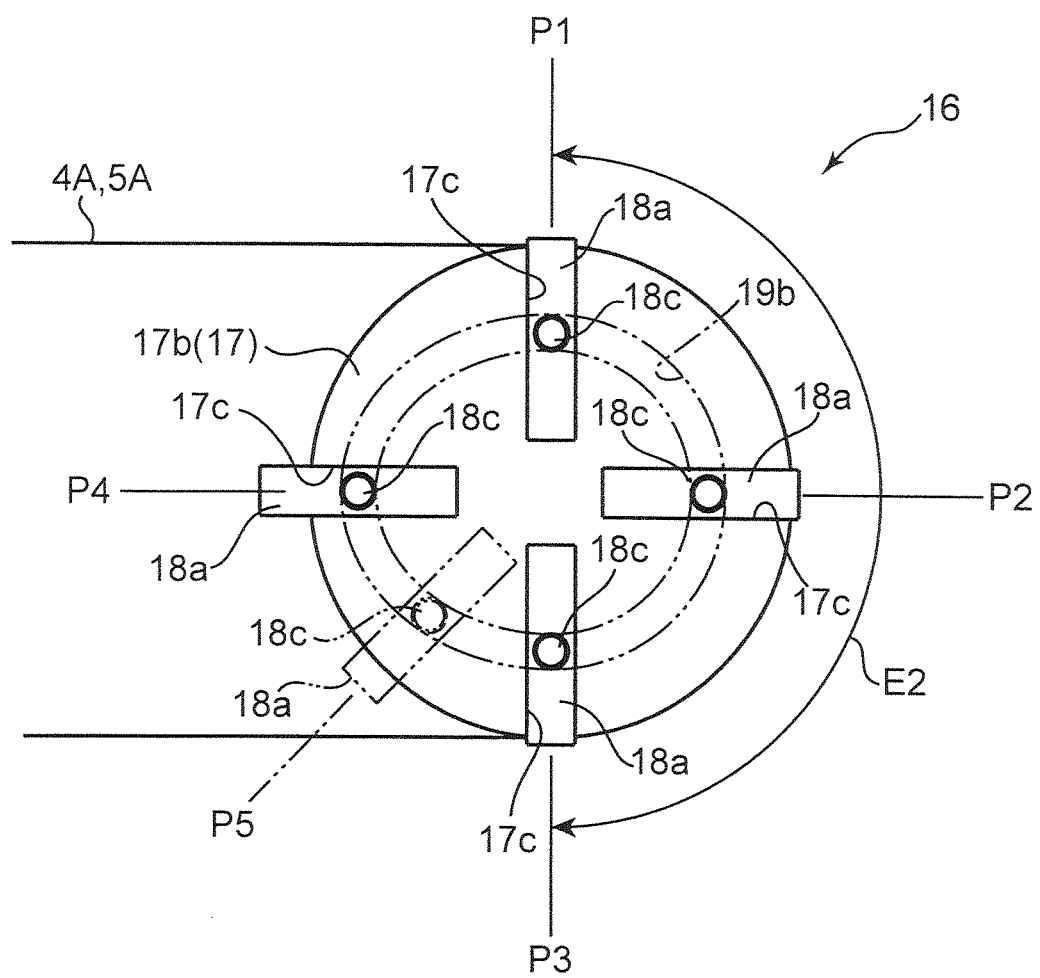
FIG. 10 is a schematic side view for explaining an operation of the holding roller in FIG. 8.

The guide members 19 are provided, respectively, at axially opposite ends of the roller body 17 (FIG. 8 illustrates one of them). Specifically, the guide member 19 comprises a guide member body 19a provided outside the rotary shaft 17a, in such a manner as to be kept stationary, irrespective of rotation of the holding barrel 17b, and a guide groove 19b formed in the guide member body 19a. The guide groove 19b supports the guide roller 18c to allow the holding portion 18b to be moved between the hold position and the release position according to rotation of the roller body 17. Specifically, as illustrated in FIG. 10, the guide groove 19b is formed in an arc shape in which a distance from a center of the holding barrel 17b becomes shortest and constant in a range E2 from a rotational position P1 to a rotational position P3 of the holding barrel 17b. That is, in the range E2, the holding portion 18b is rotated while being kept at the hold position. On the other hand, in a range where the holding barrel 17b is returned from the rotational position P3 to the rotational position P1, the guide groove 19b is formed in a curve in which the distance from the center of the holding barrel 17b becomes greater than that in the range E2. Specifically, the guide groove 19b in this embodiment is formed in a semielliptical shape in which the distance from the center of the holding barrel 17b becomes farthermost at a rotational position P4. That is, at the rotational position P4 the holding portion 18b is set at the release position.

Thus, in the range E2 from the rotational position P1 to the rotational position P3, each of the front-abdominal-portion forming strip 4A and the rear-dorsal-portion forming strip 5A is held between the holding portion 18b moved to the hold position and the outer peripheral surface of the holding barrel 17b. Then, just after passing through the rotational position P3, the holding portion 18b starts being spaced apart from the holding barrel 17b, so that the strips 4A, 5A are released. Then, at the rotational position P4, the holding portion 18b is maximally spaced apart from the holding barrel 17b. Subsequently, the holding portion 18b is returned to the rotational position P1, and moved to the hold position, again. That is, in the strip holding roller 16, the holding of the strips 4A, 5A is started at the rotational position P1, simultaneously with the dividing step (3), and the holding is released at the rotational position P3, simultaneously with the crotch portion attaching step (5).

The use of the above crotch portion attaching apparatus 11 makes it possible to implement the dividing step (3), the holding step (4) and the crotch portion attaching step (5) in a continuous process flow.

Referring to FIG. 5 again, in the folding step (6), an intermediate region of the crotch portion 3 is folded, thereby superimposing the front-abdominal-portion forming strip 4A and the rear-dorsal-portion forming strip 5A on each other.

In the side sealing step (7), the superimposed front-abdominal-portion forming strip 4A and rear-dorsal-portion forming strip 5A are joined together on a lateral side of the folded crotch portion 3 to form the side-sealed sections S1, S2.

In the cutting step (8), the superimposed the front-abdominal-portion forming strip 4A and rear-dorsal-portion forming strip 5A are cut in such a manner that the side-sealed sections S1, S2 are left, respectively, on both sides of the folded crotch portion 3.

As described above, in the production method according the above embodiment, the first attaching-detaching member 10 is attached to the front-abdominal-portion forming strip 4A to cover the dividing line D1, thereby restricting the relative displacement between the segments on both sides of the dividing line D1. Thus, it becomes possible to avoid a problem that, after the division of the front-abdominal-portion forming strip 4A, relative positions of two segments of the front-abdominal-portion forming strip 4A on both sides of the dividing line D1 are changed.

In the above production method, the subassembly is prepared before the dividing step (3), and the pair of second attaching-detaching members 6 of the subassembly is joined to the front-abdominal-portion forming strip 4A. This makes it possible to shorten a period of time from an implementation of the dividing step (3) through until relative positions of the segments on both sides of the dividing line D1 are restricted, as compared to the case where, after the dividing step (3), the pair of second attaching-detaching members 6 are joined to the front-abdominal-portion forming strip 4A, and the first attaching-detaching member 10 is attached to the second attaching-detaching members 6.

In the above production method, after joining the first attaching-detaching member 10 and the front region 3a of the crotch portion 3 together (after the first-end-region joining step), the first attaching-detaching member 10 is attached to two positions on both sides of the dividing line D1 (restricting step). This makes it possible to implement the first-end-region joining step as a part of the crotch portion forming step (2). Therefore, it becomes possible to concurrently implement the crotch portion forming step and a step implemented in association with the two segments 4A, 5A (e.g., the dividing step (3)), thereby shortening a production time, as compared to the case where the first-end-region joining step is implemented after the restricting step.

In the above production method, the restricting step and the step of joining the rear region 3b of the crotch portion 3 to the rear-dorsal-portion forming strip 5A (second-end-region joining step) are concurrently implemented. This makes it possible to shorten a production time, as compared to the case where the restricting step and the second-end-region joining step are sequentially implemented.

In the above production method, the strip holding roller 13, 16 holding thereon the front-abdominal-portion forming strip 4A and the rear-dorsal-portion forming strip 5A, and the crotch portion holding roller 14 holding thereon the crotch portion 3 provided with the subassembly, are brought into press contact with each other. That is, the strips 4A, 5A and the subassembly are pressed between the strip holding roller 13, 16 and the crotch portion holding roller 14. Thus, it becomes possible to concurrently implement the restricting step and the second-end-region joining step.

In the above production method, the front-abdominal-portion forming strip 4A is divided by bringing the dividing blade 12b into press contact with the strip holding roller 13, 16, so that the strip 4A can be divided while holding a position of the front-abdominal-portion forming strip 4A. Thus, it becomes possible to more reliably hold relative positions of two segments of the front-abdominal-portion forming strip 4A on both sides of the dividing line D1.

In the above production method, the holding step (4) is started simultaneously together with or before the dividing step (3), and discontinued simultaneously together with or after the crotch portion attaching step (restricting step in the above embodiment) (5). This makes it possible to reliably hold the front-abdominal-portion forming strip 4A divided through the dividing step (3), until the crotch portion attaching step (5) is completed.

Figure 11:
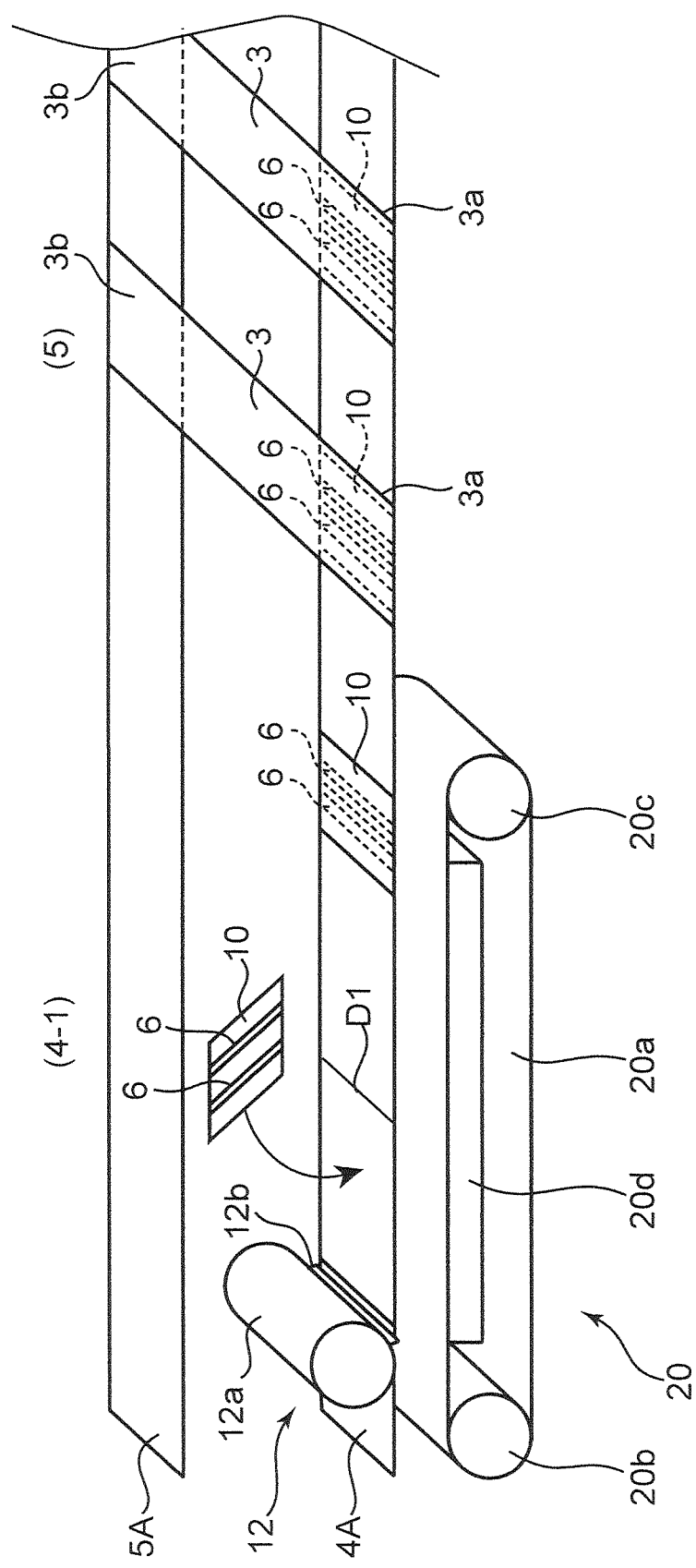
FIG. 11 is a perspective view illustrating a production method according to another embodiment of the present invention.

In the production method according to the above embodiment, after joining the subassembly of the first attaching-detaching member 10 and the pair of second attaching-detaching members 6, to the crotch portion 3 (after implementing the first-end-region joining step), the subassembly is attached to the front-abdominal-portion forming strip 4A (restricting step). Alternatively, as illustrated in FIG. 11, the restricting step may be implemented before the first-end-region joining step.

In the production method according to this embodiment, a restricting step (4-1) is implemented before the crotch portion attaching step (5).

In the restricting step (4-1), a subassembly obtained by assembling a pair of second attaching-detaching members 6 to a first attaching-detaching member 10 is prepared (preparing step). The subassembly is identical to that in the aforementioned embodiment. In the restricting step (4-1), the pair of second attaching-detaching members 6 of the subassembly are joined, respectively, to two segments of a front-abdominal-portion forming strip 4A on both sides of a dividing line D1, by an adhesive H1 (see FIG. 4, restricting step). Through this operation, the pair of second attaching-detaching members 6 are fixed to the front-abdominal-portion forming strip 4A, so that a relative displacement between the segments on both sides of the dividing line D1 is restricted by the first attaching-detaching member 10 fixedly attached to the second attaching-detaching members 6.

In the restricting step (4-1), a holding step (4) can be terminated before a crotch portion 3 larger than the first attaching-detaching member 10 is joined to the front-abdominal-portion forming strip 4A. Thus, it becomes possible to simplify a facility for the holding step (4), as compared to the case where the holding step (4) is continued until the joining of the crotch portion 3.

Specifically, in the holding step (4) in this embodiment, a holding conveyer 20 is employed.

The holding conveyer 20 comprises: an endless belt 20a for conveying the front-abdominal-portion forming strip 4A; a pair of rollers 20b, 20c circulatably supporting the endless belt 20a at two positions; and a suction member 20d disposed inside the endless belt 20a and between the rollers 20b, 20c. The endless belt 20a is a breathable (air-permeable) belt having a width dimension equal to that of the front-abdominal-portion forming strip 4A. The suction member 20d is a box-shaped member internally having a negative pressure chamber. The suction member 20d has an upper wall formed with a communication hole communicating with the negative pressure chamber. Thus, when an inside of the negative pressure chamber of the suction member 20d is depressurized by a non-illustrated suction source, the front-abdominal-portion forming strip 4A is suction-attached to the upper wall of the suction member 20d.

As above, the holding conveyer 20 may be configured to suction-hold only the front-abdominal-portion forming strip 4A, so that it can be reduced in size, as compared to the strip holding roller 13, 16.

Further, in the above embodiments, the first attaching-detaching member 10 is employed. However, the present invention is not limited thereto. For example, on an assumption that the outer surface of the crotch portion 3 is formed using a non-woven material attachable and detachable with respect to each of the second attaching-detaching members 6, the first attaching-detaching member 10 may be omitted. That is, in the sectional view of FIG. 4, the first attaching-detaching member 10 may be omitted to provide a disposable diaper configured to allow each of the second attaching-detaching members 6 and the outer surface of the crotch portion 3 to be directly attached and detached with respect to each other.

In this case, although illustration is omitted, the second attaching-detaching members 6 are joined, respectively, to two segments of the front-abdominal-portion forming strip 4A on both sides of the dividing line D1, and the front region 3a of the crotch portion 3 is detachably attached to the second attaching-detaching members 6 from thereabove (restricting step). Through this operation, a relative displacement between the segments of the front-abdominal-portion forming strip 4A on both sides of the dividing line D1 is restricted by the front region 3a of the crotch portion 3.

In this production method, the front region 3a of the crotch portion 3 is attached to the front-abdominal-portion forming strip 4A in such a manner as to cover the dividing line D1, thereby restricting the relative displacement between the segments on both sides of the dividing line D1. Thus, it becomes possible to avoid a problem that, after the division of the front-abdominal-portion forming strip 4A, relative positions of two segments of the front-abdominal-portion forming strip 4A on both sides of the dividing line D1 are changed.

Although the above embodiments have been described based on an example where the crotch portion 3 has the absorbent core, such an absorbent core may be omitted.

Further, in the above embodiments, the front-abdominal-portion forming strip 4A has described as a first strip, and the rear-dorsal-portion forming strip 5A has been described as a second strip. Alternatively, the front-abdominal-portion forming strip 4A may be served as the second strip, and the rear-dorsal-portion forming strip 5A may be served as the first strip.

The above specific embodiments primarily include an invention having the following features.

The present invention provides a method of producing a wearing article, wherein the wearing article comprises a front abdominal portion disposed on a front abdominal region of a wearer in a worn state, a rear dorsal portion disposed on a rear dorsal region of the wearer in the worn state, and a crotch portion connecting the front abdominal portion and the rear dorsal portion together in the worn state. The method comprises: an strip conveying step of conveying a first strip for forming one of the front abdominal portion and the a rear dorsal portion, and a second strip for forming the other, in such a manner as to allow respective longitudinal directions of the first and second strips to become parallel to each other, while applying, to each of the first and second strips, a tension along the longitudinal direction thereof; a dividing step of dividing the first strip being conveyed, along a dividing line along a width direction of the first strip; a holding step of holding a relative positional relationship between two segments of the first strip on both sides of the dividing line; a restricting step of, within a period of implementation of the holding step, detachably attaching a first attaching-detaching member to the first strip in such a manner as to cover the dividing line, thereby restricting a relative displacement between the segments of the first strip on both sides of the dividing line; a first-end-region joining step of joining the first attaching-detaching member and a first end region of the crotch portion together; a second-end-region joining step of joining the second strip and a second end region of the crotch portion on a side opposite to the first end region; a folding step of folding an intermediate region of the crotch portion, thereby superimposing the first and second strips on each other; a side-sealing step of joining the superimposed first and second strips together on a lateral side of the folded crotch portion; and a cutting step of cutting the superimposed first and second strips in such a manner that a joined section formed in the side-sealing step is left on each of both sides of the folded crotch portion.

The present invention makes it possible to produce a wearing article in which a front abdominal portion or rear dorsal portion (first strip) is preliminarily divided along a dividing line. In this wearing article, two segments divided along the dividing line are attachable and detachable with respect to the first strip (front abdominal portion or rear dorsal portion) through the first attaching-detaching member. Thus, a close-to-the-body fit about a wearer's waist can be adjusted only by a simple operation of detaching the divided segment(s) from the crotch portion and re-attaching the segment(s) to the crotch portion.

In production of the above wearing article, in the present invention, the first attaching-detaching member is detachably attached to the first strip to cover the dividing line, thereby restricting a relative displacement between two segments on both sides of the dividing line. Thus, it becomes possible to avoid a problem that, after the division of the first strip, relative positions of two segments on both sides of the dividing line are changed.

Thus, the present invention can provide a production method for a wearing article capable of readily adjusting a close-to-the-body fit about a wearer's waist.

Preferably, the above production method further comprises a preparing step of, before the dividing step, preparing a subassembly by assembling together the first attaching-detaching member, and a pair of second attaching-detaching members each attachable and detachable with respect to the first attaching-detaching member, wherein the restricting step includes joining the pair of second attaching-detaching members of the subassembly, respectively, to the segments of the first strip on both sides of the dividing line.

In this production method, the subassembly is prepared before the dividing step, and the pair of second attaching-detaching members of the subassembly is joined to the first strip. This makes it possible to shorten a period of time from an implementation of the dividing step through until relative positions of the segments on both sides of the dividing line D1 are restricted, as compared to the case where, after the dividing step, the pair of second attaching-detaching members are joined to the first strip, and the first attaching-detaching member is attached to the second attaching-detaching members.

Preferably, in the above production method, the restricting step is implemented after the first-end-region joining step.

In the above production method, the restricting step is implemented after the first-end-region joining step. This makes it possible to implement the first-end-region joining step as a part of a step of forming the crotch portion. Therefore, it becomes possible to concurrently implement the crotch portion forming step and a step implemented in association with the first and second strips, thereby shortening a production time, as compared to the case where the first-end-region joining step is implemented after the restricting step.

Preferably, in the above production method, the restricting step and the second-end-region joining step are concurrently implemented after the first-end-region joining step.

In this production method, the restricting step and the second-end-region joining step are concurrently implemented. This makes it possible to shorten a production time, as compared to the case where the restricting step and the second-end-region joining step are sequentially implemented.

Preferably, in the above production method, the holding step includes rotating a strip holding roller while allowing the first strip and the second strip to be held on an outer peripheral surface of the strip holding roller, and the restricting step and the second-end-region joining step include rotating a crotch portion holding roller which holds the crotch portion provided with the subassembly, while allowing an outer peripheral surface of the crotch portion holding roller to be brought into press contact with the outer peripheral surface of the strip holding roller.

In this production method, the strip holding roller holding the first and second strips, and the crotch portion holding roller holding the crotch portion provided with the subassembly, are brought into press contact with each other. That is, the first and second strips and the crotch portion provided with the subassembly are pressed between the strip holding roller and the crotch portion holding roller. Thus, it becomes possible to concurrently implement the restricting step and the second-end-region joining step.

Preferably, in the above production method, the dividing step includes rotating a dividing roller having a dividing blade formed on an outer peripheral surface thereof, in such a manner that the dividing blade is brought into press contact with the strip holding roller with a constant cycle.

In this production method, the first strip is divided by bringing the dividing blade into press contact with the strip holding roller, so that the first strip can be divided while holding a position of the first strip. Thus, it becomes possible to more reliably hold relative positions of two segments of the first strip on both sides of the dividing line.

In the above production method, the restricting step is implemented before the first-end-region joining step.

In this production method, the restricting step is implemented before the first-end-region joining step. This makes it possible to allow the holding step to be terminated before the crotch portion larger than the first attaching-detaching member is joined to the first strip. Thus, it becomes possible to simplify a facility for the holding step, as compared to the case where the holding step is continued until the joining of the crotch portion.

The present invention also provides a method of producing a wearing article, wherein the wearing article comprises a front abdominal portion disposed on a front abdominal region of a wearer in a worn state, a rear dorsal portion disposed on a rear dorsal region of the wearer in the worn state, and a crotch portion connecting the front abdominal portion and the rear dorsal portion together in the worn state. The method comprises: an strip conveying step of conveying a first strip for forming one of the front abdominal portion and the a rear dorsal portion, and a second strip for forming the other, in such a manner as to allow respective longitudinal directions of the first and second strips to become parallel to each other, while applying, to each of the first and second strips, a tension along the longitudinal direction thereof; a dividing step of dividing the first strip being conveyed, along a dividing line along a width direction of the first strip; a holding step of holding a relative positional relationship between two segments of the first strip on both sides of the dividing line; a restricting step of, within a period of implementation of the holding step, detachably attaching a first end region of the crotch portion to the first strip in such a manner as to cover the dividing line, thereby restricting a relative displacement between the segments of the first strip on both sides of the dividing line; a second-end-region joining step of joining a second end region of the crotch portion on a side opposite to the first end region to the second strip; a folding step of folding an intermediate region of the crotch portion, thereby superimposing the first and second strips on each other; a side-sealing step of joining the superimposed first and second strips together on a lateral side of the folded crotch portion; and a cutting step of cutting the superimposed first and second strips in such a manner that a joined section formed in the side-sealing step is left on each of both sides of the folded crotch portion.

The present invention makes it possible to produce a wearing article in which a front abdominal portion or rear dorsal portion (first strip) is preliminarily divided along a dividing line. In this wearing article, two segments divided along the dividing line are attachable and detachable with respect to the first end region of the crotch portion. Thus, a close-to-the-body fit about a wearer's waist can be adjusted only by a simple operation of detaching the divided segment(s) from the crotch portion and re-attaching the segment(s) to the crotch portion.

In production of the above wearing article, in the present invention, the first end region of the crotch portion is detachably attached to the first strip to cover the dividing line, thereby restricting a relative displacement between two segments on both sides of the dividing line. Thus, it becomes possible to avoid a problem that, after the division of the first strip, relative positions of two segments on both sides of the dividing line are changed.

Thus, the present invention can provide a production method for a wearing article capable of readily adjusting a close-to-the-body fit about a wearer's waist.

Preferably, in the above production method, the holding step is started simultaneously together with or before the dividing step, and discontinued simultaneously together with or after the restricting step.

This makes it possible to reliably hold the first strip divided through the dividing step, until the restricting step is completed.

The present invention further provides a wearing article produced by the above production method.

Furthermore, the present invention provides a wearing article which comprises: a front abdominal portion disposed on a front abdominal region of a wearer in a worn state; a rear dorsal portion disposed on a rear dorsal region of the wearer in the worn state; and a crotch portion having a front end region connected to the front abdominal portion and a rear end region connected to the rear dorsal portion, in the worn state, wherein the front abdominal portion or the rear dorsal portion has a dividing line along which the front abdominal portion or the rear dorsal portion is preliminarily divided into a right segment and a left segment, and wherein each of the right and left segments is attachable and detachable with respect to the front or rear end region of the crotch portion.

In the present invention, the front abdominal portion or the rear dorsal portion is preliminarily divided into a right segment and a left segment along the dividing line, and each of the right and left segments is attachable and detachable with respect to the crotch portion. Thus, a close-to-the-body fit about a wearer's waist can be adjusted only by a simple operation of detaching the right segment and/the left segment from the crotch portion and re-attaching the segment(s) to the crotch portion.

What is claimed is:

1. A method of producing a wearing article, wherein the wearing article comprises a front abdominal portion disposed on a front abdominal region of a wearer in a worn state, a rear dorsal portion disposed on a rear dorsal region of the wearer in the worn state, and a crotch portion connecting the front abdominal portion and rear dorsal portion together in the worn state, the method comprising:

a strip conveying step of conveying a first strip for forming one of the front abdominal portion and the rear dorsal portion, and a second strip for forming the other, in such a manner as to allow respective longitudinal directions of the first and second strips to become parallel to each other, while applying, to each of the first and second strips, a tension along the longitudinal direction thereof;

a dividing step of dividing the first strip being conveyed, along a dividing line along a width direction of the first strip;

a holding step of holding a relative positional relationship between two segments of the first strip on both sides of the dividing line;

a restricting step of, within a period of implementation of the holding step, detachably attaching a first attaching-detaching member to the first strip in such a manner as to cover the dividing line, thereby restricting a relative displacement between the segments of the first strip on both sides of the dividing line;

a first-end-region joining step of joining the first attaching-detaching member and a first end region of the crotch portion together;

a second-end-region joining step of joining the second strip and a second end region of the crotch portion on a side opposite to the first end region;

a folding step of folding an intermediate region of the crotch portion, thereby superimposing the first and second strips on each other;

a side-sealing step of joining the superimposed first and second strips together on a lateral side of the folded crotch portion;

a cutting step of cutting the superimposed first and second strips in such a manner that a joined section formed in the side-sealing step is left on each of both sides of the folded crotch portion; and a preparing step of, before the dividing step, preparing a subassembly by assembling together the first attaching-detaching member, and a pair of second attaching-detaching members each attachable and detachable with respect to the first attaching-detaching member, wherein the restricting step includes joining the pair of second attaching-detaching members of the subassembly, respectively to the segments of the first strip on both sides of the dividing line, the restricting step being implemented after the first-end-region joining step.

2. The method of producing a wearing article according to claim 1, wherein the restricting step and the second-end-region joining step are concurrently implemented after the first-end-region joining step.

3. The method of producing a wearing article according to claim 2, wherein the holding step includes rotating a strip holding roller while allowing the first strip and the second strip to be held on an outer peripheral surface of the strip holding roller, and the restricting step and the second-end-region joining step include rotating a crotch portion holding roller which holds the crotch portion provided with the subassembly, while allowing an outer peripheral surface of the crotch portion holding roller to be brought into press contact with the outer peripheral surface of the strip holding roller.

4. The method of producing a wearing article according to claim 3, wherein the dividing step includes rotating a dividing roller having a dividing blade formed on an outer peripheral surface thereof, in such a manner that the dividing blade is brought into press contact with the strip holding roller with a constant cycle.

5. The method of producing a wearing article according to claim 1, wherein the restricting step and the second-end-region joining step are concurrently implemented after the first-end-region joining step.

6. The method of producing a wearing article according to claim 5, wherein the holding step includes rotating a strip holding roller while allowing the first strip and the second strip to be held on an outer peripheral surface of the strip holding roller, and the restricting step and the second-end-region joining step include rotating a crotch portion holding roller which holds the crotch portion provided with the subassembly, while allowing an outer peripheral surface of the crotch portion holding roller to be brought into press contact with the outer peripheral surface of the strip holding roller.

* * * * *